United States Patent
Chekroun et al.

Patent Number: 5,476,941
Date of Patent: Dec. 19, 1995

[54] 2-[2-(5-TETRAZOLYL)PHENYL]-1,2-DIHYDROQUINOLINE DERIVATIVES

[75] Inventors: Isaac Chekroun, Epinay; José Ruiz-Montes, Mantes la Jolie; Guy Rossey, Voisins le Bretonneux, all of France

[73] Assignee: Synthelabo, Le Plessis Robinson, France

[21] Appl. No.: 320,404

[22] Filed: Oct. 3, 1994

[30] Foreign Application Priority Data

Oct. 4, 1993 [FR] France ................ 93 11772

[51] Int. Cl.⁶ .................... C07D 215/04
[52] U.S. Cl. ........................ 546/173
[58] Field of Search ............. 546/167, 173

[56] References Cited

U.S. PATENT DOCUMENTS 5,371,227  12/1994  Cremer et al. ............. 546/174

FOREIGN PATENT DOCUMENTS 0528762  2/1993  European Pat. Off. .
0529452  3/1993  European Pat. Off. .
0540400  5/1993  European Pat. Off. .
0569013  11/1993  European Pat. Off. .

*Primary Examiner*—Jane Fan
*Attorney, Agent, or Firm*—Jacobson, Price, Holman & Stern

[57] ABSTRACT

A compound of formula (1):

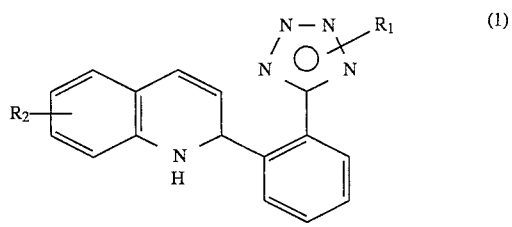

in which
  $R_1$ represents a 1,1-dimethylethyl, triphenylmethyl, methoxymethyl or benzyloxymethyl group; and
  $R_2$ represents a $C_1$–$C_4$ alkyl group.

4 Claims, No Drawings

2-[2-(5-TETRAZOLYL)PHENYL]-1,2-DIHYDROQUINOLINE DERIVATIVES

The subject of the present invention is 2-[2-(5-tetrazolyl)phenyl]-1,2-dihydroquinoline derivatives, their preparation and their use as synthesis intermediates.

The present invention provides a compound of formula (1):

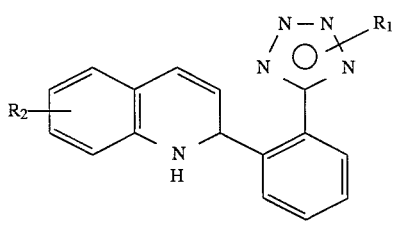

in which:

R₁ represents a 1,1-dimethylethyl, triphenylmethyl, methoxymethyl or benzyloxymethyl group; and R₂ represents a $C_1$–$C_4$ alkyl group.

R₁ is preferably in position 1 or 2 on the tetrazolyl group. R₁ is also preferably a 1,1-dimethylethyl or triphenylmethyl group. R₂ is preferably in position 6 on the dihydroquinoline group. R₂ may be, for example, a methyl, ethyl, i-propyl, n-propyl, n-butyl, i-butyl or t-butyl group.

The compounds according to the invention may be prepared according to Scheme 1.

A metal phenyltetrazole of formula (2) in which R₁ is as defined above and M represents potassium, lithium, sodium or magnesium, is reacted with a quinoline of formula (3) in which R₂ is as defined above, and a compound of formula (1) is obtained. The reaction takes place in an aprotic solvent such as tetrahydrofuran or 1,2-dimethoxyethane, pure or mixed with hexane, cyclohexane or toluene. The reaction takes place, for instance, at a temperature of from room temperature to the reflux temperature.

Scheme 1

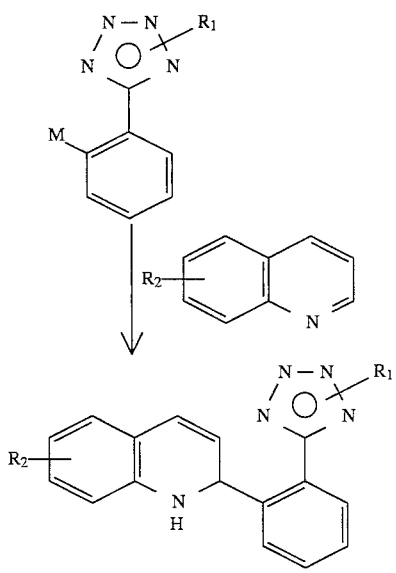

The starting compounds are commercially available or are described in the literature or may be prepared according to the methods which are described therein or which are known to a person skilled in the art.

Thus, the compounds of formula (2) in which M represents lithium may be prepared from 5-phenyltetrazole in the following way: the tetrazolyl group of 5-phenyltetrazole is protected by a 1,1-dimethylethyl group according to the method described for an analogous derivative by J. W. Tilley et al., J. Med. Chem. 1991, 34, 1125–1126, and the compound obtained is reacted with an alkyllithium such as butyllithium, in an aprotic solvent such as tetrahydrofuran, at a temperature of from −50° C. to 66° C.

The Example which follows illustrates the invention. The microanalyses and the IR and NMR spectra confirm the structure of the compounds obtained.

EXAMPLE

2-{2-[2-(1,1-Dimethylethyl)-2H-tetrazol-5-yl]phenyl}-6-methyl-1,2-dihydroquinoline 1. 2-(1,1-Dimethylethyl)-5-phenyl-2H-tetrazole.

30 g of 5-phenyltetrazole and 210 ml of trifluoroacetic acid are introduced into a 500 ml round-bottomed flask. 10 ml of concentrated sulphuric acid and 33.6 g of 1,1-dimethylethanol are added to the suspension obtained. The reaction mixture is left stirring for 48 hours and is then poured onto 750 ml of ethyl acetate. The solution is washed with twice 200 ml of water and then with 10% sodium hydroxide until the pH is alkaline, and again with twice 200 ml of water. After drying the organic phase and evaporation under vacuum, 36.15 g of product are obtained in oil form.

This product has the same characteristics as that described by R. A. Henry, J. Heterocyclic Chem., 1976, 13, 391–392.

2. 2-{2-[2-(1,1-Dimethylethyl)-2H-tetrazol-5-yl]phenyl}-6-methyl-1,2-dihydroquinoline 100 g (490 mmol) of 2-(1,1-dimethylethyl)-5-phenyl-2H-tetrazole and 500 ml of anhydrous tetrahydrofuran are introduced into a 2-liter three-necked round-bottomed flask under a nitrogen atmosphere. 215 ml (580 mmol) of 2.5M n-butyllithium solution in hexane are added dropwise to the mixture. The mixture is heated at the reflux temperature for 45 minutes, followed by addition of 49 g (410 mmol) of 6-methylquinoline dissolved in 300 ml of toluene. The reaction medium is left for 2 hours at the reflux temperature and is then cooled to room temperature. Next, 300 ml of ethanol are added and the solvent is evaporated off under reduced pressure. The residue is taken up in 500 ml of water and is filtered, washed with 200 ml of isopropanol and dried under vacuum.

132.5 g of product are obtained in the form of pale yellow crystals, which product is used as it is.

Melting point=164°–166° C.

The compounds of the invention are particularly useful for the synthesis of compounds of formula (I)

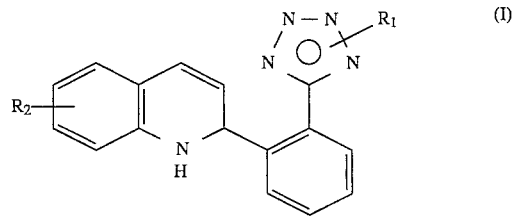

in which R₁ and R₂ are as defined above.

The compounds of formula (I) are obtained by oxidation of the 1,2-dihydroquinoline ring of the compounds of formula (1). Thus, the oxidation reaction may, for example, be performed either in the presence of manganese dioxide in a solvent such as toluene or xylene at a temperature of from room temperature to the reflux temperature, or in the presence of potassium permanganate in a solvent such as ethyl acetate at the reflux temperature, or in the presence of sodium hypochlorite, or in the presence of hydrogen peroxide, or in the presence of palladium on charcoal in a solvent such as toluene or xylene at a temperature of from 100° C. to the reflux temperature, or in the presence of nitrobenzene at a temperature of from 100° C. to 170° C.

Example A below illustrates the use of the compounds of formula (1) for the synthesis of the compounds of formula (I).

Example A

2-{2-[2-(1,1-Dimethylethyl)- 2H-tetrazol-5-yl)phenyl]-6methylquinoline

Route a:

5 g (14.4 mmol) of 2-{2-[2-( 1,1-dimethylethyl)-2H-tetrazol-5-yl]phenyl}- 6-methyl-1,2dihydroquinoline and 2.51 g (28.9 mmol) of manganese dioxide in 50 ml of toluene are successively introduced into a 100 ml three-necked round-bottomed flask. The reaction medium is heated for 2 hours at 80° C. and is then allowed to return to room temperature. The reaction medium is filtered over Celite and evaporated to dryness. 4.94 g of product are obtained in the form of white crystals.
Melting point=103°–105° C.
Route b:

1 g (2.9 mmol) of 2-{2-[2-( 1,1-dimethylethyl)-2H-tetrazol-5-yl]phenyl}- 6-methyl-1,2dihydroquinoline, 0.91 g (5.8 mmol) of potassium permanganate and 20 ml of ethyl acetate are successively introduced into a 50 ml three-necked round-bottomed flask. The reaction medium is brought to the reflux temperature and is heated for 1 hour. The mixture is allowed to cool to room temperature and is filtered over Celite, washed with 20 ml of 10% sodium bisulphite solution, dried over magnesium sulphate and evaporated to dryness.

0.99 g of product is obtained in the form of white crystals.
Melting point=103°–105° C.
Route c:

3.5 g (10 mmol) of 2-{2-[2-( 1,1-dimethylethyl)-2H-tetrazol-5-yl]phenyl}- 6-methyl-1,2dihydroquinoline, and 20 ml of nitrobenzene are successively introduced into a 100 ml three-necked round-bottomed flask. The reaction medium is heated for 1 hour at 170° C. and is then allowed to return to room temperature. The mixture is subsequently diluted with 100 ml of toluene and is washed successively with 50 ml of 10% hydrochloric acid solution and then with 50 ml of concentrated hydrochloric acid solution. The phases are separated and the pH of the aqueous phase is adjusted to 12 with 30% sodium hydroxide solution and is extracted 3 times with 50 ml of toluene. The organic phases are subsequently combined, washed successively with 15 ml of water and then with 15 ml of saturated sodium chloride solution and the solvent is evaporated off.

2.95 g of product are obtained in the form of white crystals.
Melting point=103°–105° C.
Route d:

5.9 g (17 mmol) of 2-{2-[2-( 1,1-dimethylethyl)-2H-tetrazol-5-yl]phenyl}- 6-methyl-1,2-dihydroquinoline, 1 g of 5% palladium on charcoal and 50 ml of toluene are successively introduced into a 100 ml three-necked round-bottomed flask. The mixture is heated for 3 hours at 80° C. and is then allowed to return to room temperature. The reaction medium is subsequently filtered over Celite and the solvent is then evaporated off.

5.84 g of product are obtained in the form of white crystals.
Melting point=103°–105° C.
Route e:

10 g (29 mmol) of 2-{2-[2-( 1,1-dimethylethyl)-2H-tetrazol-5-yl]phenyl}- 6-methyl-1,2-dihydroquinoline, 0.1 g of benzyltriethylammonium chloride, 100 ml of 48% sodium hypochlorite solution in water and 80 ml of toluene are successively introduced into a 100 ml three-necked round-bottomed flask. The reaction medium is heated at the reflux temperature for 20 hours and is then allowed to cool to room temperature. The phases are separated and the organic phase is collected. The organic phase is subsequently washed successively with 50 ml of 10% sodium bisulphite solution in water and then with 50 ml of saturated sodium chloride solution and dried over magnesium sulphate, and the solvent is evaporated to dryness.

9.3 g of product are obtained in the form of white crystals.
Melting point=103°–105° C.

Compounds of formula (I) are described in EP-A-0,540, 400, EP-A-0,569,013, EP-A-0,604,259 and FR-A-92/08, 201.

These compounds of formula (I) are useful as intermediates in the synthesis of compounds which are antagonists of angiotensin II, such as those described in EP-A-0,528,762, EP-A-0,540,400, EP-A-0,569,013, EP-A-0,604,259 and FR-A-92/08,201.

We claim:
1. A compound of formula (1):

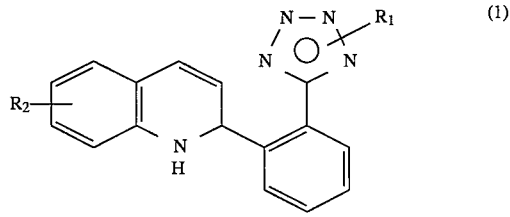

in which $R_1$ represents a 1,1-dimethylethyl, triphenylmethyl, methoxymethyl or benzyloxymethyl group; and $R_2$ represents a $C_1$–$C_4$ alkyl group.

2. A compound according to claim 1 wherein $R_1$, in position 1 or 2 on the tetrazolyl group, represents a 1,1-dimethylethyl or triphenylmethyl group.

3. A compound according to claim 1 wherein $R_2$ is in position 6 on the dihydroquinoline group.

4. 2-{2-[2-(1,1-Dimethylethyl)- 2H-tetrazol-5-yl]phenyl}-6-methyl- 1,2-dihydroquinoline.

* * * * *